United States Patent [19]

Wells et al.

[11] Patent Number: 5,729,018
[45] Date of Patent: Mar. 17, 1998

[54] AIR CRYSTAL AND ASSEMBLY FOR INFRARED MICROSPECTROSCOPY

[75] Inventors: Simon A Wells, Wendover; David Gosbee, Leighton Buzzard, both of England

[73] Assignee: Perkin-Elmer Ltd., Beaconsfield, England

[21] Appl. No.: 608,653

[22] Filed: Feb. 29, 1996

[30] Foreign Application Priority Data

Mar. 3, 1995 [EP] European Pat. Off. ............ 95301402

[51] Int. Cl.⁶ .................................................. G01N 21/01
[52] U.S. Cl. .................... 250/339.08; 250/339.07
[58] Field of Search ........................ 250/339.08, 339.11, 250/339.07, 341.8; 359/350, 385

[56] References Cited

U.S. PATENT DOCUMENTS

| 5,093,580 | 3/1992 | Sting | 250/571 |
|---|---|---|---|
| 5,172,182 | 12/1992 | Sting | 356/244 |
| 5,200,609 | 4/1993 | Sting . | |

FOREIGN PATENT DOCUMENTS 0529999  3/1993  European Pat. Off. .

*Primary Examiner*—Kiet T. Nguyen
*Attorney, Agent, or Firm*—David Aker

[57] ABSTRACT

An ATR crystal (40) for use in microscopy has a conical portion (65) for contacting a sample under investigation. The apex of the cone can be provided with a small flat surface which enables reliable and reproducible ATR analysis to be undertaken. An assembly is for mounting such a crystal.

10 Claims, 7 Drawing Sheets

VIEW MODE

AIR MEASUREMENT

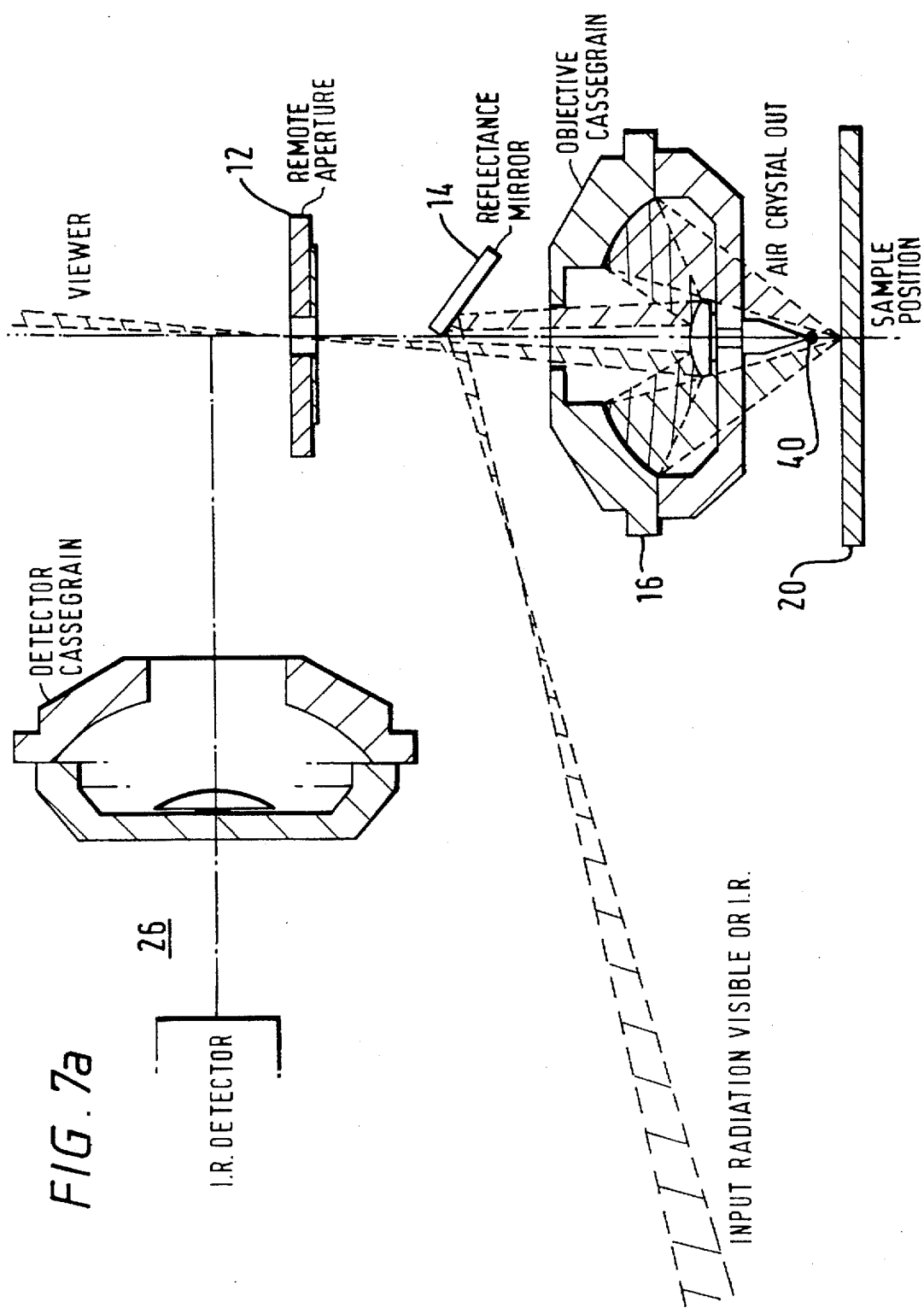

AIR CRYSTAL AND ASSEMBLY FOR INFRARED MICROSPECTROSCOPY

FIELD OF THE INVENTION

This invention relates to apparatus for carrying out spectroscopic analysis of samples. Such apparatus typically includes a source of visible radiation and a source of radiant energy in the non-visible wavelength range, typically radiation in the infrared (IR) range. The infrared radiation is used to undertake spectroscopic analysis of the sample.

BACKGROUND ART

A known apparatus of this type is an FT-IR microscope such as that manufactured by Perkin-Elmer. This type of microscope can be used to analyse very small samples. The sample can be mounted on a stage between an objective lens and a condenser lens. In general terms the microscope can be used in either a transmitting mode or a reflecting mode. The reflecting mode is usually employed when the sample under investigation is non-transmitting to the analysing radiation. The microscope is usually used in conjunction with an IR spectrophotometer to obtain an IR spectrum of the sample.

When poorly reflecting samples are analysed in the reflecting mode it is known to use what is called the attenuated total reflection (ATR) technique. In this, a crystal which utilises total internal reflection or attenuated total internal reflection, is located in contact with the sample during the analysis step. Contact between the sample and the crystal is usually maintained by the application of pressure. Conventionally the crystals have been of a hemispherical shape with the lower surface of the hemisphere being in contact with the sample. Examples of apparatus making use of such crystals are described in U.S. Pat. No. 5,093,580, JP-A-4-348254 and JP-A-5-164972. The crystals are usually made of an infrared transmitting material such as ZnSe or germanium. In some prior art apparatus the crystals are mounted so that they can be moved out of contact with the sample in order to permit visual observation of the sample during a setting-up stage.

With the crystal in its removed position the sample is viewed e.g. through an optical microscope and the area of interest identified and positioned appropriately. The crystal is then brought into contact with the sample and then analysed with the microscope in its infrared mode.

There are two significant problems with the conventional arrangements which make use of hemispherical crystals. One is uncertainty concerning the actual area of the sample being analysed and the other is creating sufficient pressure between the crystal and the sample at the area of contact in order to obtain a reliable measurement.

SUMMARY OF THE INVENTION

The present invention is concerned with an apparatus in which these problems are alleviated.

One aspect of the present invention provides an ATR type crystal for use in apparatus for carrying out spectroscopic analysis which comprises a crystal body which has an upper body portion through which analysing radiation can pass towards a sample to be analysed, and a generally conical lower part whose apex in use is in contact with the sample.

The upper body portion may be part spherical and the radiation may pass therethrough substantially without refraction.

By means of such an arrangement it is possible to create a relatively small, flat surface at the apex of the cone to provide a known area of contact with the sample. Furthermore, because the area provided by the apex of the cone is relatively small the crystal can be used to develop a high pressure contact between the sample and crystal without increasing the area of contact.

The crystal body may have a flat upper surface to allow bonding to a support. The contact surface of the apex will have dimensions usually in the range 50 microns to 200 microns, with a typical value being of the order of 100 microns.

Another aspect of the present invention provides a mounting assembly for an ATR type crystal which comprises a frame having generally radially extending limbs attachable to an objective lens of an apparatus for carrying out spectroscopic analysis, an axially depending support element carried by said frame, said support element including first and second relatively movable members, the second of which carries on its lower end an ATR type crystal of the type defined in said one aspect, and means biasing said second member to its lowermost position and means allowing movement of the second member upwardly against said bias means.

The second member may be located axially within an outer tubular first member so that said members can undergo relative axial movement. The ATR type crystal may be secured by adhesive to the lower end of the second member. The bias means may comprise a spring disposed within the upper portion of the first tubular member. The support means may include means permitting adjustment of the bias exerted by the spring on the second member.

Such a mounting assembly may be provided as an attachment for an existing apparatus for carrying out spectroscopic analysis such as the FT-IR microscope.

BRIEF DESCRIPTION OF THE DRAWINGS

The invention will be described now by way of example only, with particular reference to the accompanying drawings. In the drawings:

FIG. 7a is a side schematic view showing the ATR crystal in its position during viewing of the sample;

DETAILED DESCRIPTION OF THE PREFERRED EMBODIMENT

Figure 1:
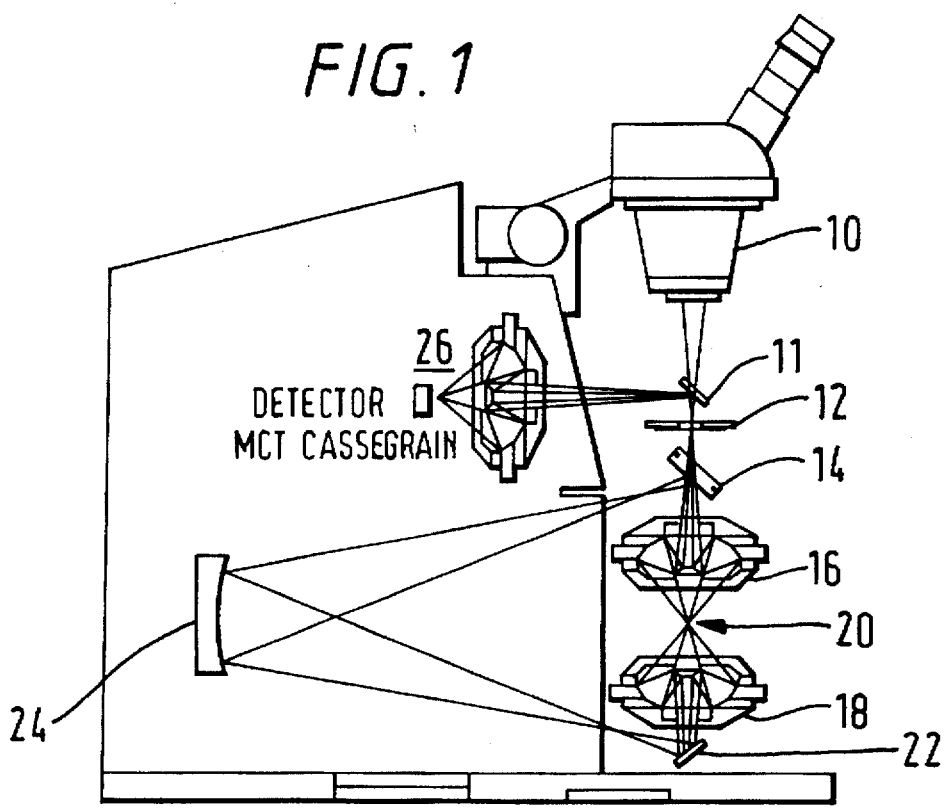
FIG. 1 is a schematic side view illustrating the principal elements of an FT-IR microscope.

FIG. 1 shows the principal elements of an FT-IR microscope such as that manufactured by Perkin-Elmer. The microscope includes an optical microscope (10) which is disposed above a view/IR mirror (11) which in turn is disposed above a remote aperture (12). Below the remote aperture (12) is located a transmittance/reflectance mirror (14) which is positioned above an objective Cassegrain assembly (16) and a condenser Cassegrain assembly (18). Between the two Cassegrains is disposed a sample position (20) usually a stage. Below the condenser Cassegrain (18) there is a flat mirror (22) which can direct radiation from a toroid coupling optic (24) which in turn is configured to receive radiation from a radiation source, typically a visible radiation source or an infrared radiation source. The apparatus also includes a detector and an MCT Cassegrain arrangement (26) which is used to carry out the spectroscopic analysis in conjunction with an IR spectrophotometer (not shown).

It will be appreciated that the microscope includes a source of visible radiation and can also be coupled to a source of infrared radiation which usually is contained in an associated spectrophotometer. These sources are not shown on FIG. 1.

Those skilled in the art will appreciate the manner in which such a microscope operates and a full explanation of this operation is not required for purpose of understanding the present invention. A fuller description of the microscope can be found in an article entitled an FTIR microscope by D. W. Shearing, E. F. Young, and T. P. Byron published in American Laboratory, November 1990 and also in the user's manual of The Perkin-Elmer FT/IR microscope.

Figure 2:
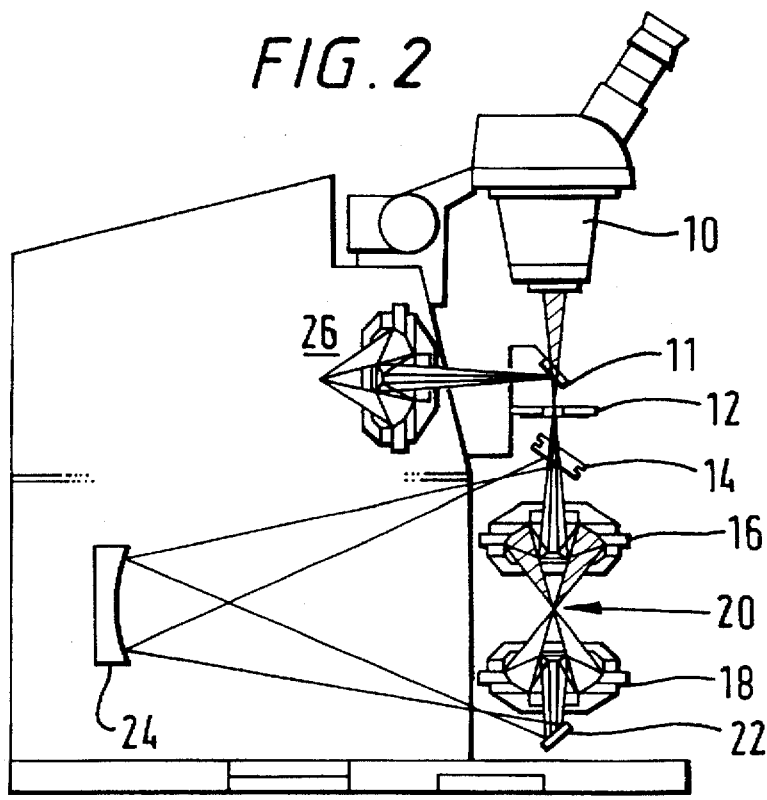
FIGS. 2 and 3 are views similar to FIG. 1 illustrating the operation of the microscope.

Briefly, it will be appreciated that a first step in analysing a sample using a microscope of the type shown in FIG. 1 is viewing the sample to identify the area to be investigated. The configuration of the microscope during sample viewing is shown in FIG. 2. In this arrangement an input beam of radiation from the visible light source is directed towards the reflectance mirror (14) and reflected towards the objective Cassegrain (16). From the Cassegrain the light beam passes to the sample position and light is returned via the objective Cassegrain to the optical microscope (10).

Figure 3:
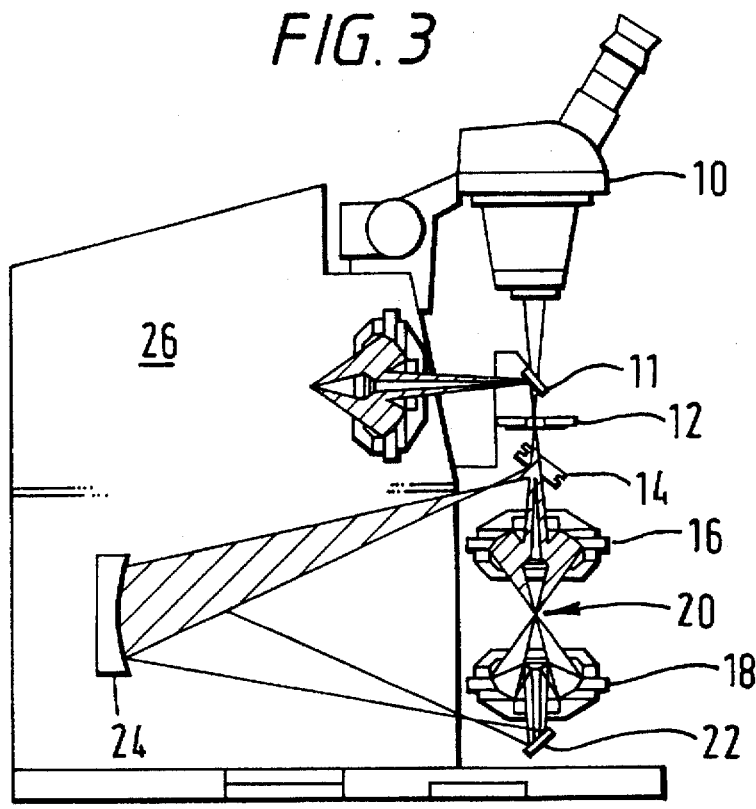

Once the sample has been positioned correctly on its stage, a standard reflectance measurement can then be undertaken and the configuration in this mode is illustrated in FIG. 3. The input beam of analysing radiation again passes towards the reflectance mirror (14) and through the objective Cassegrain (16) towards the sample position (20). From the sample the beam is reflected upwardly via the objective Cassegrain through the remote aperture (12) to the mirror (11). It needs to be noted that the mirror (11) is a movable element which is not in its operative position during the viewing configuration of FIG. 2, but is placed in that position for the analysis. From the mirror (11) the beam is directed towards the detecting arrangement, which enables spectroscopic analysis to be undertaken.

Figure 4:
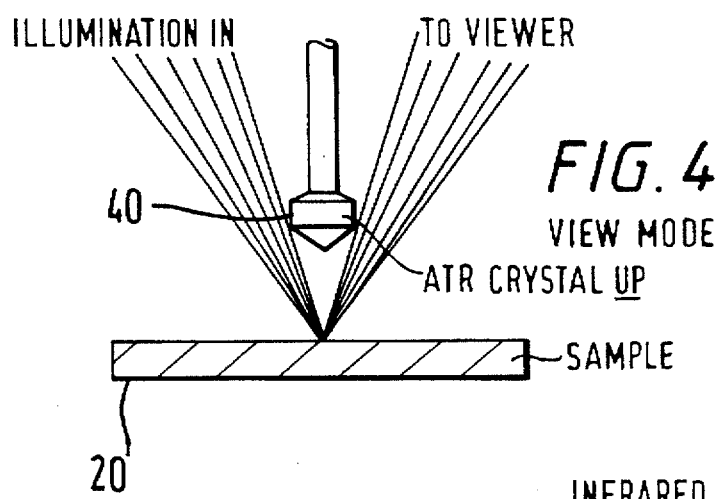
FIGS. 4 and 5 are schematic views showing the ATR technique.
Figure 5:
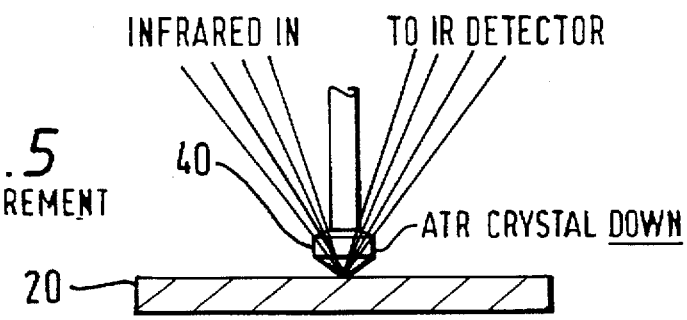

It will be further appreciated that the configuration of the microscope as shown in FIG. 2 is its reflectance mode. When a poorly reflecting sample is under investigation it is known to make use of an ATR crystal which is supported intermediate the objective Cassegrain and the sample. FIGS. 4 and 5 are views equivalent to FIGS. 2 and 3 illustrating the position of the ATR crystal (40) during sample viewing (FIG. 4) and during an actual analysis measurement (FIG. 5). During the analysis measurement the crystal is in contact with the sample and the basic principles upon which the crystal operates will be appreciated by those skilled in the art.

Figure 6A:
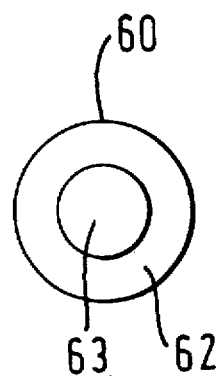
FIGS. 6a to 6c are, respectively, plan, side and bottom views of an ATR crystal in accordance with the present invention.
Figure 6B:
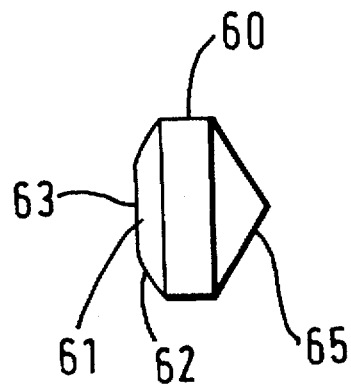
Figure 6C:
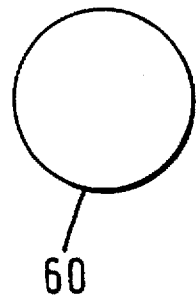
Figure 8:
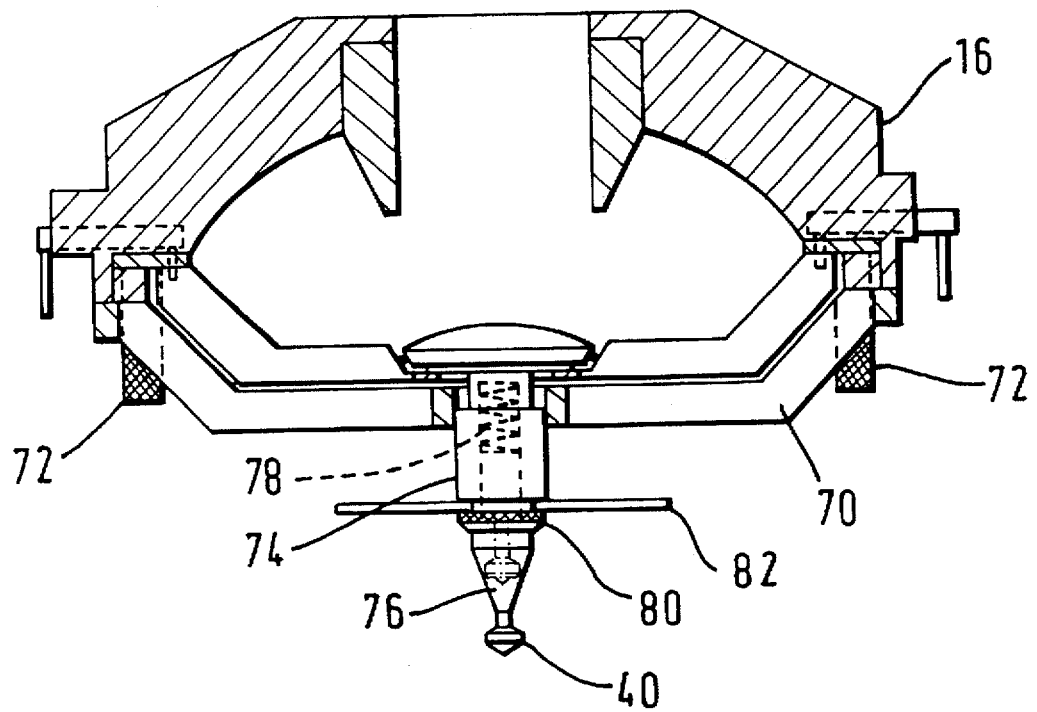
FIG. 8 is a side view of a mounting assembly for an ATR crystal.

The present arrangement is concerned with the particular form of the ATR crystal employed. The crystal is shown in detail in FIGS. 6a to 6c. The crystal comprises a cylindrical intermediate portion (60), an upper portion (61) having a part spherical surface (62) and a flat top (63) and a lower generally conical portion (65). The crystal typically is formed from a material which transmits infrared radiation, e.g. germanium or silicon. Approximate dimensions of the crystal are as follows. The radius of the intermediate portion (60) is of the order of 2 mm, the total axial extent of the crystal is of the order of 3 mm and the apex (66) of the cone is formed with a small flat surface whose dimensions are typically 100 microns, but can be in the range of approximately 50 microns to 200 microns.

Figure 7B:
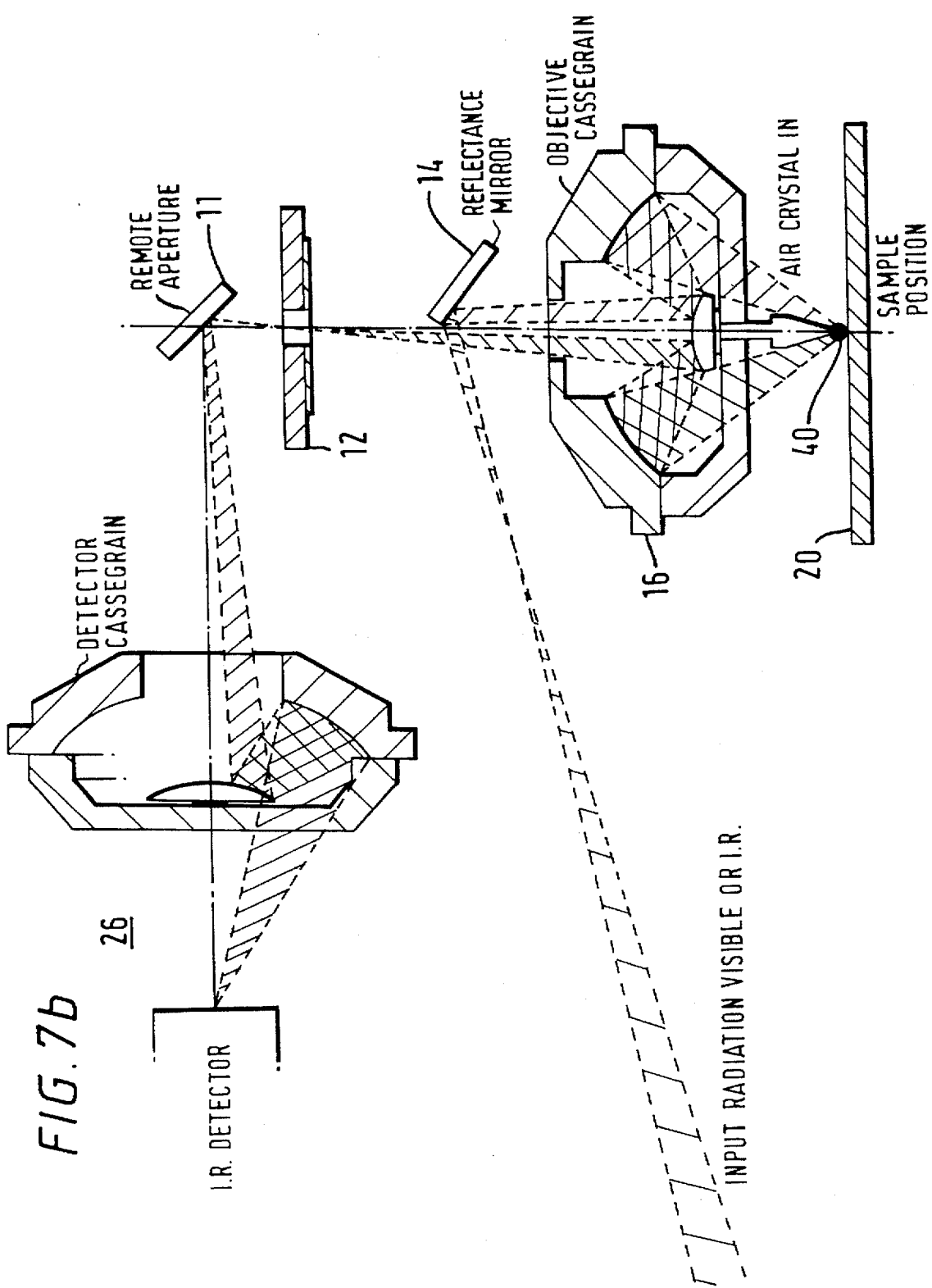
FIG. 7b is a view similar to FIG. 7a showing the crystal in its position during a measurement step.
Figure 9:
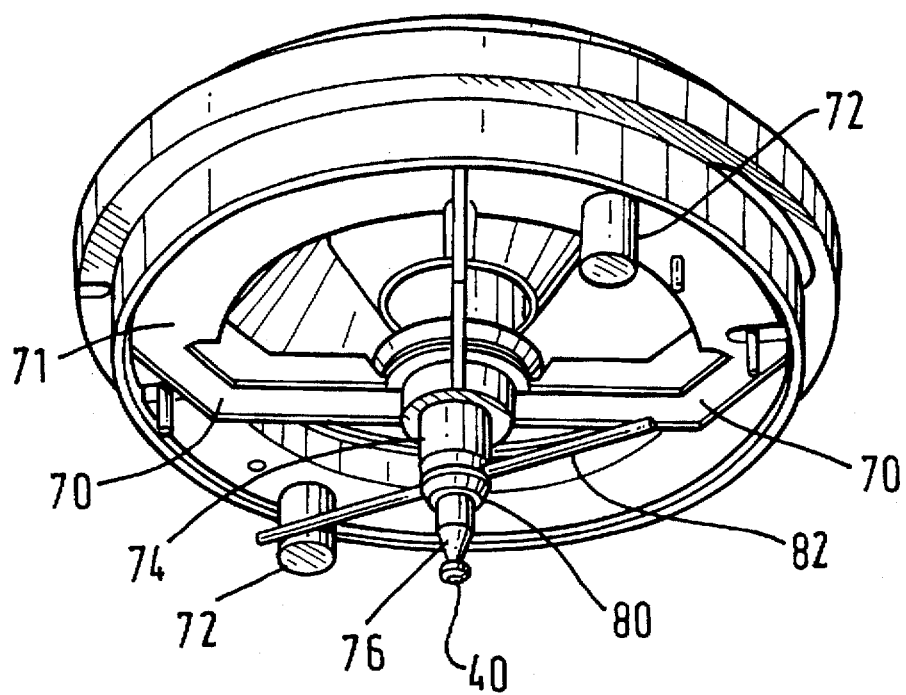
FIG. 9 is a perspective view from below of the mounting assembly.
Figure 11:
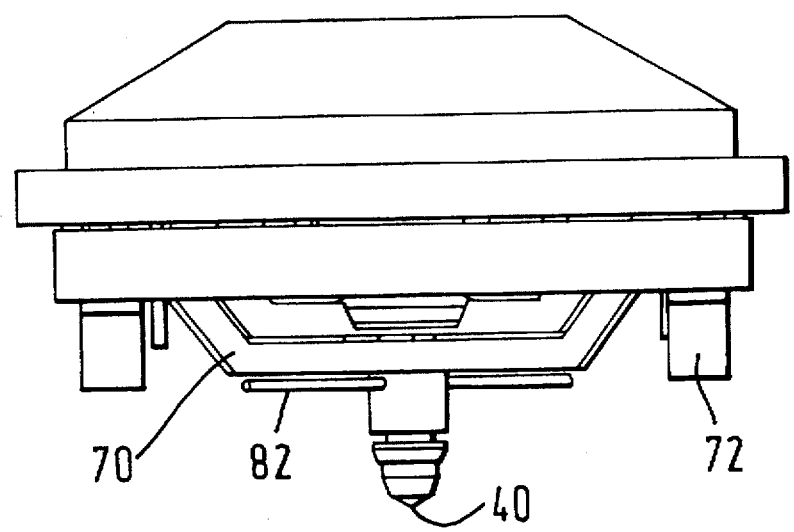
FIG. 11 is a side elevation of the mounting assembly with the crystal in its raised position.
Figure 10:
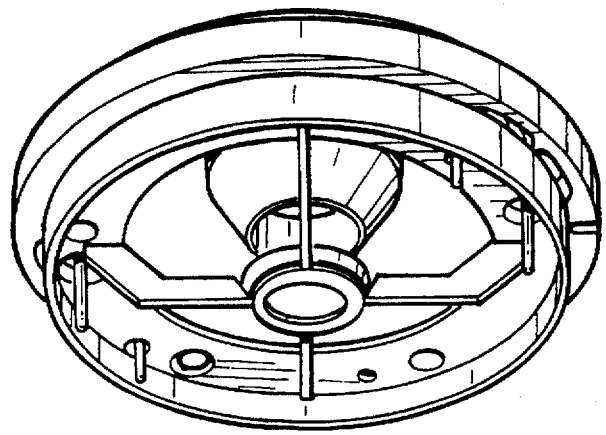
FIG. 10 is an exploded view of the mounting assembly.
Figure 10:
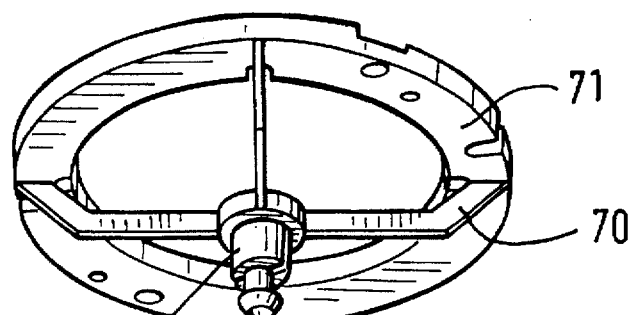
Figure 10:
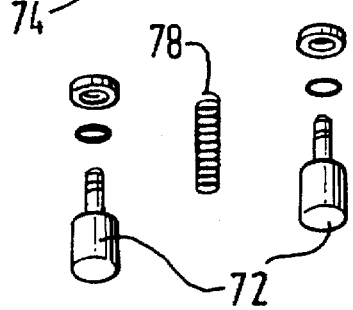
Figure 10:
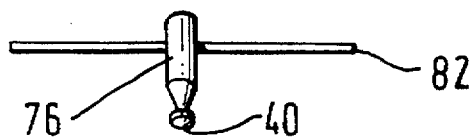
Figure 10:
Figure 10:

In the present arrangement it is proposed to support the crystal from the Cassegrain objective in the manner illustrated in FIGS. 4 and 5. FIGS. 7a and 7b illustrate in more detail the position of the crystal (40) during the viewing and measurement modes. As can be seen in the viewing mode the visible radiation does not pass through the crystal whilst in the measurement mode it does. The spherical surface (62) is shaped such that incident radiation is substantially normal to the surface (62) and thus passes through without refraction. Of significance is the fact that only the flat face of the apex of the conical portion is in contact with the sample under investigation. The significance of this is that it provides a known area of contact in a specific and reproducible manner for a large variety of samples. Furthermore, the use of the relatively small area enables a relatively high pressure contact to be formed between the sample and crystal without any increase in the contact area between them. This assists in obtaining reliable measurements. Because of the reproducibility of position and area of the sample and the contact pressure, the design of crystal gives higher sampling reproducibility for ATR spectroscopy.

The crystal (40) can be incorporated into a mounting assembly of the type shown in FIGS. 8 to 11 of the drawings. This assembly can be incorporated into existing spectroscopic apparatus such as the FT-IR microscope. The arrangement shown in FIGS. 8 to 11 is designed to fit into the Perkin-Elmer FT/IR microscope and, in particular, to be attached to the objective Cassegrain (16) of that microscope. The mounting assembly includes a frame structure having radially extending limbs (70) connected to a ring (71), the frame structure being coupled to the Cassegrain objective at angularly spaced peripheral positions by means of screw connectors (72). At a central position the frame structure supports a downwardly extending mounting assembly which comprises an outer tubular member (74) within which is located an axially movable member (76). The axially movable member has a tapering lower portion which carries at its lower extremity the crystal (40) shown in FIG. 6. A spring (78) is located within the tubular member (74) and acts to bias the inner member downwardly. A nut (80) engages the outer threaded portion of the second member and can be used to adjust the axial position of the crystal. The crystal can be raised and lowered by means of a manually operable toggle bar (82) which can be manually operated to move the second member upwardly or downwardly.

The inner and outer members (74 and 76) are coupled by a bayonet type coupling in which a radially outwardly projecting pin on the inner member (76) engages in a slot in the outer member (76). To move the crystal to an upper position the toggle is pushed upwardly to move the member (76) upwardly against the spring bias. The toggle bar is then twisted so that bayonet connection maintains that position in a manner similar to a light bulb connection. To lower the crystal the toggle bar (82) is twisted to release the bayonet connection and the member (76) can then fall to its lower position.

We claim:

1. A mounting assembly for an ATR type crystal which comprises a frame having generally radially extending limbs attachable to an objective lens of an apparatus for carrying out spectroscopic analysis, an axially depending support element carried by said frame, said support element including first and second relatively movable members, the second of which carries on its lower end an ATR type crystal and means biasing said second member to its lowermost position and means allowing movement of the second member upwardly against said bias means.

2. A mounting assembly according to claim 1, wherein the second member is located axially within an outer tubular first member so that said members can undergo relative axial movement.

3. A mounting assembly according to claim 1, wherein the ATR type crystal is secured by adhesive to the lower end of the second member.

4. A mounting assembly according to claim 1, wherein the bias means comprises a spring disposed within the upper portion of the first tubular member.

5. A mounting assembly according to claim 4, wherein the support means includes means permitting adjustment of the bias exerted by the spring on the second member.

6. A mounting assembly according to claim 1, wherein the ATR crystal comprises a crystal body which has an upper body portion through which analysing radiation can pass towards a sample to be analysed, and a generally conical lower part whose apex in use is in contact with the sample.

7. A mounting assembly according to claim 6, wherein the upper body portion is a part spherical and the radiation can pass therethrough substantially without refraction.

8. A mounting assembly according to claim 7, wherein the crystal body has a flat upper surface to allow bonding to a support.

9. A mounting assembly according to claim 6, wherein the crystal body has a flat upper surface to allow bonding to a support.

10. A mounting assembly according to claim 6, wherein the contact surface at the apex of the conical part has dimensions usually in the range 50 microns to 200 microns, with a typical value being of the order of 100 microns.

* * * * *